United States Patent [19]

Stuetz

[11] Patent Number: 5,132,459

[45] Date of Patent: Jul. 21, 1992

[54] PROPENYLAMINES, PROCESSES FOR THEIR PRODUCTION, PHARMACEUTICAL COMPOSITIONS CONTAINING THEM AND THEIR USE AS PHARMACEUTICALS

[75] Inventor: Anton Stuetz, Maria Enzersdorf, Austria

[73] Assignee: Sandoz Ltd., Basel, Switzerland

[21] Appl. No.: 384,237

[22] Filed: Jul. 21, 1989

Related U.S. Application Data

[60] Continuation of Ser. No. 209,747, Jun. 21, 1988, abandoned, which is a division of Ser. No. 646,724, Sep. 4, 1984, Pat. No. 4,755,534, which is a continuation of Ser. No. 233,559, Feb. 11, 1981, abandoned, which is a continuation-in-part of Ser. No. 180,207, Aug. 21, 1980, abandoned.

[51] Int. Cl.⁵ .............................. C07C 45/00
[52] U.S. Cl. ........................ 564/387; 564/501
[58] Field of Search .......................... 564/387

[56] References Cited

U.S. PATENT DOCUMENTS 4,755,534 7/1988 Stuetz .................... 564/387

Primary Examiner—Jane T. Fan
Assistant Examiner—Raymond Covington
Attorney, Agent, or Firm—Gerald D. Sharkin; Robert S. Honor; Thomas O. McGovern

[57] ABSTRACT

Compounds of formula I

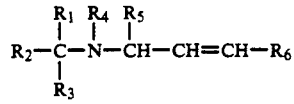

wherein $R_1$ represents a group of formula

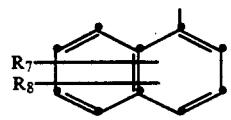

IIa

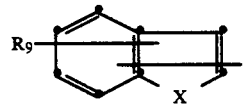

IIb

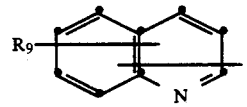

IIc

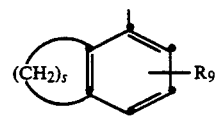

IId

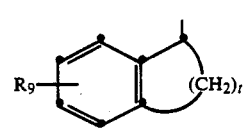

IIe

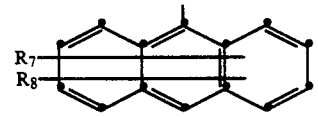

IIf

8 Claims, No Drawings

PROPENYLAMINES, PROCESSES FOR THEIR PRODUCTION, PHARMACEUTICAL COMPOSITIONS CONTAINING THEM AND THEIR USE AS PHARMACEUTICALS

This is a continuation of application Ser. No. 07/209,747, filed Jun. 21, 1988 now abandoned, which in turn is a division of application Ser. No. 06/646,724, filed Sep. 4, 1984, now U.S. Pat. No. 4,755,534, which in turn is a continuation of application Ser. No. 06/233,559, filed Feb. 11, 1981, now abandoned, which in turn is a continuation-in-part of application Ser. No. 06/180,207, filed Aug. 21, 1980, now abandoned.

This invention relates to propenylamines, processes for their production, pharmaceutical compositions containing them and their use as pharmaceuticals.

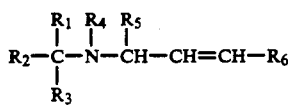
I wherein
a) $R_1$ represents a group of formula

IIa

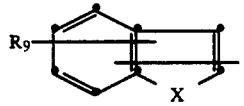
IIb

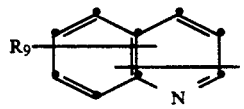
IIc

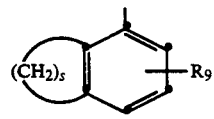
IId

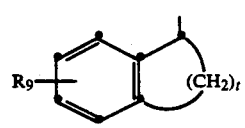
IIe

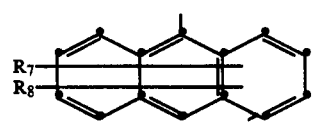
IIf or

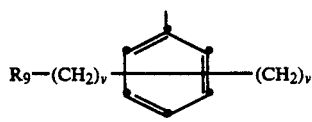
IIg and $R_2$ represents hydrogen or lower alkyl,
or $R_1$ and $R_2$ together represent a group of formula

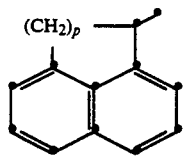
IIh

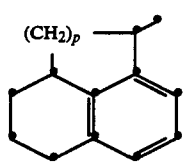
IIi whereby in the formulae IIa to IIi, $R_7$ and $R_8$ represent, independently, hydrogen, halogen, trifluoromethyl, hydroxy, nitro, lower alkyl or lower alkoxy, $R_9$ represents hydrogen, halogen, hydroxy, lower alkyl or lower alkoxy, X represents oxygen, sulphur, imino, lower alkyl imino or a radical of formula $-(CH_2)_r-$, p is 1, 2 or 3,
r is 1, 2 or 3,
s is 3, 4 or 5,
t is 2, 3 or 4, and
v is 3, 4, 5 or 6;

$R_3$ and $R_5$ represent, independently, hydrogen or lower alkyl, and $R_4$ represents $C_{1-6}$alkyl or $C_{3-8}$ cycloalkyl-$(C_{1-6})$-alkyl; and $R_6$ represents a group of formula

IIIa

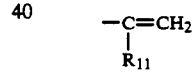
IIIb or

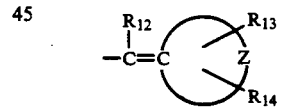
IIIc wherein
$R_{11}$ represents hydrogen, optionally α-hydroxy substituted alkyl; alkenyl, alkynyl, cycloalkyl, cycloalkylalkyl, phenyl, phenalkyl or thienyl, $R_{12}$, $R_{13}$ $R_{14}$ represent, independently, hydrogen or lower alkyl, and

represents a $C_{5-8}$ cycloalkylidene radical optionally containing a double bond; or b) $R_1$ represents a group of formula IIa to IIg as defined under a), $R_2$ represents hydrogen or lower alkyl, $R_3$ and $R_4$ together form a group $-(CH_2)_u-$, wherein u is an integer of 1 to 8, and $R_5$ and $R_6$ have the meanings given under a).

Any lower alkyl or lower alkoxy radical has preferably 1 to 4 carbon atoms, especially 2 or 1 carbon atoms. Unless otherwise stated alkyl moieties preferably have 1 to 12 carbon atoms especially 2 to 8 carbon atoms, particularly 2 to 6 carbon atoms and most preferably 3 to 5 carbon atoms and if bridging 1 to 4 particularly 1 or 2 carbon atoms. Any alkenyl or alkynyl radical has preferably 3 to 6 carbon atoms, especially 3 or 4 carbon atoms, e.g. allyl, propenyl or propynyl. Such alkyl, alkoxy, alkenyl and alkinyl groups can be straight-chain or branched. A preferred cycloalkylidene radical is cyclohexylidene. The term cycloalkyl is to be understood as including polycyclo groups such as bornyl or adamantyl but is preferably cyclohexyl or cyclopentyl.

Conveniently $R_7$ and $R_8$ are identical and are both hydrogen. Conveniently $R_9$ is hydrogen or halogen. In IIb and IIc the bond to the carbon atoms to which $R_2$ and $R_3$ are attached is conveniently attached meta to X and para to the ring nitrogen, respectively. X is conveniently sulphur, imino or lower alkylamino. $R_1$ is preferably a radical of formula IIb, IIc or IId, or especially IIa. $R_2$ is preferably hydrogen. $R_3$ is preferably hydrogen and $R_4$ is conveniently alkyl. $R_5$ is conveniently hydrogen.

The values of p, r, s, t, u and v are conveniently chosen to produce a seven- preferably a five- or six-membered ring.

The double bond between $R_6$ and the nitrogen atom preferably has the trans-configuration.

Halogen stands for fluorine, chlorine or bromine, preferably chlorine or bromine.

The present invention also provides a process for the production of a compound of formula I, which comprises a) when $R_6$ represents a group of formula IIIa, as defined above, (compound Ia), reacting a compound of formula IV,

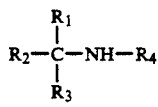

wherein $R_1$ to $R_4$ are as defined above, with a compound of formula V,

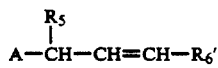

wherein A is a leaving group, $R_5$ is as defined above, and $R_6'$ stands for a group of formula IIIa, as defined above, or b) when $R_6$ represents a group of formula IIIa, wherein $R_{11}$ represents α-hydroxyalkyl (compounds Ib), reacting a metalated compound of formula Ic,

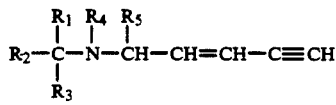

wherein $R_1$ to $R_5$ are as defined above, with a carbonyl compound of formula VII,

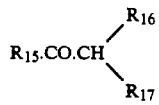

wherein $R_{15}$, $R_{16}$ and $R_{17}$ represent independently hydrogen or lower alkyl, or c) when the double bond between $R_6$ and the nitrogen atom is in trans configuration (compounds Id) reducing a compound of formula VIII,

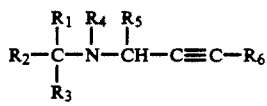

wherein $R_1$ to $R_6$ are as defined above, with diisobutylaluminiumhydride, or d) when $R_6$ represents a group of IIIb or IIIc as defined above or a group of formula IIId,

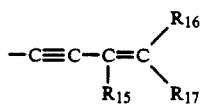

wherein $R_{15}$, $R_{16}$ and $R_{17}$ are as defined above (compounds Ie) splitting off water from a compound of formula

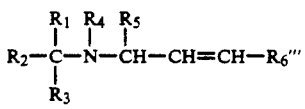

wherein $R_1$ to $R_5$ are as defined above, and $R_6'''$ represents a group of formula IIIe, IIIf, or IIIg,

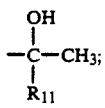

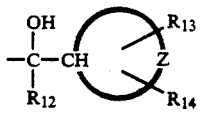

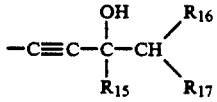

wherein $R_{11}$ to $R_{17}$ and Z are as defined above, or e) when $R_3$ represents hydrogen or lower alkyl and $R_4$ represents $C_{1-6}$alkyl or $C_{3-8}$cycloalkyl-$(C_{1-6})$-alkyl (compounds Ig), introducing the group $R_4'$ into a compound of formula IX,

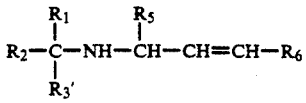

wherein $R_1$, $R_2$, $R_5$ and $R_6$ are as defined above, $R_3'$ represents hydrogen or lower alkyl, and $R_4'$ represents $C_{1-6}$alkyl or $C_{3-8}$cycloalkyl-$(C_{1-6})$-alkyl.

Process a) may be effected in conventional manner for the production of tertiary amines by condensation from analogous starting materials. The process may be effected in an inert solvent such as a lower alkanol, e.g. ethanol, optionally in aqueous admixture, an aromatic hydrocarbon solvent, e.g. benzene or toluene, a cyclic ether, e.g. dioxane or a carboxylic acid dialkylamide solvent, e.g. dimethylformamide. The reaction temperature is conveniently from room temperature to the boiling temperature of the reaction mixture, preferably room temperature. The reaction is conveniently effected in the presence of an acid binding agent, such as an alkali metal carbonate, e.g. sodium carbonate. The leaving group A is conveniently iodine or preferably chlorine or bromine, or an organic sulphonyloxy group having 1 to 10 carbon atoms, e.g. alkylsulphonyloxy, preferably having 1 to 4 carbon atoms such as mesyloxy, or alkylphenylsulphonyloxy preferably having 7 to 10 carbon atoms such as tosyloxy.

Process b) may be effected in conventional manner, for example by metalating the compound of formula Ic, e.g. with butyllithium in an inert solvent such as an ether e.g. tetrahydrofuran and subsequently reacting the metalated compound of formula Ic, thus obtained, preferably without isolation with a compound of formula VII.

The reduction with diisobutylaluminium hydride (DIBAH) according to process c) is preferably carried out in an inert solvent e.g. in an aromatic hydrocarbon such as toluene or benzene and at room temperature or raised temperature e.g. 35° to 40° C.

The splitting-off of water according to process d) can be carried out with a suitable agent such as an inorganic acid, e.g. hydrochloric or sulphuric acid, an organic acid, e.g. methanesulphonic acid, benzenesulphonic acid or p-toluenesulphonic acid or an inorganic or organic acid anhydride or -halide e.g. $POCl_3$ in an inert solvent. An excess of an acid halide if used can act as reaction medium whereby the reaction is carried out in the presence of an acid binding agent such as a tertiary amine, e.g. a trialkylamine or pyridine. Reaction temperatures vary according to reaction conditions and lie for example between $-10°$ and 180° C. The splitting-off of water can also be carried out with the help of polyphosphoric acid at temperatures between 80° and 120° whereby inorganic acids such as phosphoric acid, organic acids such as acetic acid or an excess of polyphosphoric acid can serve as solvent.

Process e) may be effected in manner conventional for the "alkylation" of secondary amines (the term "alkylation" being used here to denote introduction of any of the hydrocarbyl groups $R_4$), for example by direct "alkylation" with an "alkylating" agent, for example a halide or sulphate, or by reductive alkylation, in particular by reaction with an appropriate aldehyde and subsequent or simultaneous reduction. Reductive "alkylation" is suitably effected by reacting a compound of formula IX in an inert organic solvent, such as a lower alkanol, e.g. methanol, and at an elevated temperature, in particular at the boiling temperature of the reaction mixture with the corresponding aldehyde. The subsequent reduction may be effected with, for example, a complex metal hydride reducing agent, e.g. $NaBH_4$ or $NaCNBH_3$. The reduction may also be effected simultaneously to the alkylation, for example by use of formic acid which may serve both as reducing agent and as reaction medium. The reaction is preferably carried out at raised temperature, in particular at the boiling point of the reaction mixture.

Free base forms of the compounds of formula I may be converted into salt forms and vice versa. Suitable acid addition salts are e.g. hydrochloride, hydrogen fumarate or naphthaline-1,5-disulphonate.

The compounds of the formula I and their intermediate can be obtained in the form of isomeric mixtures of the various cis/trans isomers which can be separated according to established methods. Alternatively, isomers of the compounds can be obtained by using the appropriate isomer of the starting material. Unless otherwise stated the compounds are always to be understood as being mixtures of these isomers.

The starting materials of formula IV are in part new and can be prepared by reacting in conventional manner a compound of formula X,

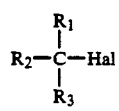    X with a compound of formula XI, $R_4$—$NH_2$    XI wherein in the formulae X and XI $R_1$ to $R_4$ are as defined above and Hal stands for halogen.

The starting materials of formula V are in part new and can be prepared by reacting a compound of formula XII, $R_6'H$    XII according to the following scheme

whereby $R_6'$, $R_5$ and A are as defined above and $Me^\oplus$ represents a metal cation.

The starting materials of formula VIII are new and can be prepared a') by subjecting a compound of formula IV, defined above, and compounds of formulae XVI and XVII

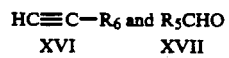

to a Mannich reaction or b') in the case when $R_6$ represents a group of formula IIIa as defined above by reacting a compound of formula IV as defined above with a compound of formula XVIII.

to give a compound of formula XIX,

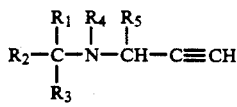 XIX and subjecting this to a Cadiot-Chodkiewicz coupling reaction with Cu+ and a compound of formula XX, R₆'Hal   XX or c') when R₆ represents a group of formula IIIb as defined above splitting off water from a compound of formula XXI,

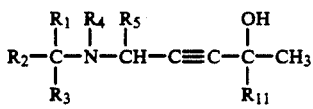 XXI whereby in the formulae XVI to XXI R₁ to R₆, R₆', R₁₁, A and Hal are as defined above.

The starting materials of formula IX are new and can be prepared for example by reacting a compound of formula XXII,

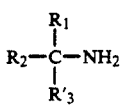 XXII with a compound of formula XXIII

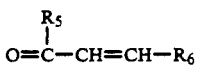 XXIII to give a compound of formula XXIV

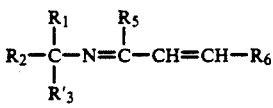 XXIV and reducing this e.g. with a complex hydride such as NaBH₄, whereby in the formulae XXII to XXIV R₁, R₂, R₃', R₅ and R₆ are as defined above.

Compounds of formula XXI can be prepared a") by subjecting a compound of formula IV as defined above, a compound of formula XVII as defined above, and a compound of formula XXV,

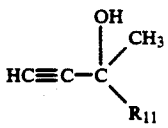 XXV to a Mannich reaction, or b") metalating a compound of formula XIX, as defined above, and reacting the metal compound thus obtained with a carbonyl compound of formula XXVI,

CH₃.CO.R₁₁   XXVI whereby in the formulae XXV and XXVI R₁₁ is as defined above.

The compounds of formulae IVa and IVb

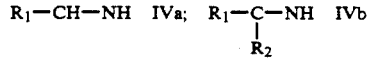

can be prepared according to the following scheme

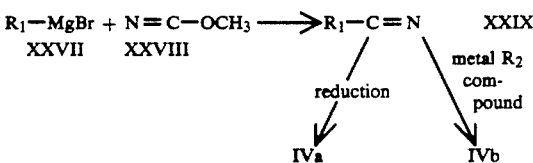

whereby in the formulae IVa, IVb and XXVII to XXIX R₁, R₂ and u are as defined above.

The starting materials of formula If wherein R₆''' represents a group of formula IIIe or IIIf as defined above are new and can be prepared by reduction with LiAlH₄ of a compound of formula XXIa,

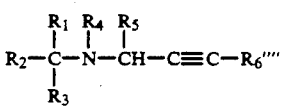 XXIa wherein R₁ to R₅ are as defined above and R₆'''' represents a group of formula IIIe or IIIf as defined above.

Compounds of formula XX are in part new and can be prepared by reacting a compound of formula XII, as defined above, with butyllithium and a halogen.

The new compounds of formulae IV, V, VIII, IX XX and If also form part of the invention. The remaining intermediate compounds are either known or can be prepared according to known methods or as hereinbefore described.

The compounds of formula I are useful because they possess chemotherapeutic activity. In particular, they are useful as antimycotic agents, as indicated in vitro in various families and types of mycetes, including Trichophyton spp, Asperigillus spp, Microsporum spp and *Sporotrychium schenkii* and Candida spp at concentrations of, for example 0.01 to 100 μg/ml, and in vivo in the experimental skin mycosis model in guinea pigs. In this model, guinea pigs are infected by subcutaneous applications of *Trichophyton quinckeanum*. The test substance is administered daily for 7 days beginning 24 hours after the infection either by local application by rubbing the test substance (taken up in polyethylene glycol) on the skin surface, or per orally or sub-cutaneously, the test substance being administered as a suspension. The activity is shown on local application at concentrations of for example 0.01 to 5%. The oral activity is shown in vivo in the guinea pig—Trichophytosis model at dosages of, for example 2 to 70 mg/kg.

For the above-mentioned use, the dose administered will of course vary depending on the compound employed, mode of administration and treatment desired. However, in general, satisfactory results are obtained when administered at a daily dosage of from 1 to 100 mg/kg of animal body weight, conveniently given in divided doses two to four times daily, or in sustained release form. For the larger mammals, the corresponding daily dosages are in the range of from 70 to 2000 mg, and dosage forms suitable for oral administration comprise from 17.5 to 1000 mg. The invention therefore also concerns a method of treating diseases or infections caused by mycetes using a compound of formula I.

The compounds may be used in free base form or in the form of chemotherapeutically acceptable acid addition salts. Such salt forms exhibit the same order of activity as the free base forms. Suitable salt forms are e.g. hydrochloride, hydrogen fumarate or naphthaline-1,5-disulphonate.

The compounds may be admixed with conventional chemotherapeutically acceptable diluents and carriers, and, optionally, other excipients and administered in such forms as tablets or capsules. The compounds may alternatively be administered topically in such conventional forms as ointments or creams or parenterally. The concentrations of the active substance will of course vary depending on the compound employed, the treatment desired and the nature of the form etc. In general, however, satisfactory results are obtained e.g. in topical application forms at concentrations of from 0.05 to 5, in particular 0.1 to 1 wt %.

Such compositions also form part of the invention. Examples of preferred compound groups are (i) compounds of formula I wherein $R_6$ represents a group of formula IIIa wherein $R_{11}$ represents alkyl preferably $C_2$-$C_8$alkyl, more preferably $C_2$-$C_6$alkyl, most preferably $C_3$-$C_5$alkyl for example n- or in particular t-butyl;

(ii) compounds of formula I wherein $R_6$ represents a group of formula IIIa wherein $R_{11}$ represents α-hydroxy substituted alkyl; alkenyl, alkynyl, cycloalkyl, cycloalkylalkyl, phenyl, phenalkyl or thienyl;

(iii) compounds of formula I wherein $R_{11}$ represents alkyl, alkenyl, alkynyl, cycloalkylalkyl, phenyl or phenalkyl and all other substituents are as defined under formula I;

(iv) compounds of formula I wherein
   a) $R_1$ represents a group of the formula IIa, IIb, IIe,
   $R_2$ represents hydrogen,
   $R_3$ represents hydrogen,
   $R_4$ represents lower alkyl,
   $R_5$ represents hydrogen or lower alkyl, or
   $R_3$ and $R_4$ together form a group —$(CH_2)_u$— or
   b) wherein $R_1$ and $R_2$ together represent a group of the formula IIh,
   $R_3$ represents hydrogen,
   $R_4$ represents lower alkyl,
   $R_5$ represents lower alkyl and
   $R_6$ is as hereinbefore defined, whereby within these groups $R_6$ is preferably a group of formula IIIa as hereinbefore defined or as described under (i) or (ii) above and/or $R_1$ is preferably a group of formula IIa.

Preferred meanings of the substituents in the compounds of the formula I are such as set out hereinbefore.

Compounds of formula I are generally preferred wherein the double bond between $R_6$ and the nitrogen atom is in trans-configuration.

Particularly preferred individual compounds are: N-methyl-N-(1-naphthylmethyl)-non-2(trans)-en-4-ynyl-1-amine and N-methyl-N-(1-naphthylmethyl)-6,6-dimethyl-hept-2(trans)-en-4-ynyl-1-amine, and their hydrochlorides.

The following Examples illustrate the invention whereby all temperatures are in degrees centigrade.

EXAMPLE 1 trans-N-(3-Benzo[b]thiophenemethyl)-N-methyl-non-2-en-4-ynyl-1amine and
cis-N-(3-Benzo[b]thiophenemethyl)-N-methyl-non-2-en-4-ynyl-1-amine [process a)]

12 g 1-Bromo-2-nonen-4-yne (cis/trans mixture) are added dropwise to a mixture of 10.5 g N-(3-Benzo[b]thiophenemethyl)-N-methylamine, 8.2 g $K_2CO_3$ and 100 ml dimethylformamide and stirred overnight. The reaction mixture is filtered and the solvent removed under vacuum. The residue is partitioned between ether and saturated aqueous $NaHCO_3$, the organic phase dried, concentrated under vacuum and chromatographed over kieselgel using toluene/ethylacetate 4:1 as eluant. The trans isomer is eluted first followed by the cis isomer. Both are oils.

EXAMPLE 2 trans-N-Methyl-N-(1-naphthylmethyl)-6-hydroxy-6-methylhept-2-en-4-ynyl-1-amine [process b)]

10.7 ml of a 15% butyllithium solution in hexane are added dropwise to 3 g of trans N-methyl-N-(1-naphthylmethyl)pent-2-en-4-ynyl-1-amine in absolute tetrahydrofuran and reacted after 30 minutes with a solution of 1.79 g of acetone. The reaction mixture is stirred for 24 hours at room temperature, poured onto ice and extracted with chloroform. The organic phase is washed, dried and concentrated under vacuum. After chromatography over kieselgel (eluant toluene/ethyl acetate 4:1) the title compound is obtained as an oil.

EXAMPLE 3 a)

trans-N-Methyl-N-(1-naphthylmethyl)-non-2-en-4-ynyl-1-amine [process c)]

72 ml of a 1.2M solution of DIBAH in toluene are added dropwise to a solution of 5 g N-methyl-N-(1-naphthylmethyl)-2,4-nonadiynyl-1-amine in dry toluene and the resulting mixture stirred under protective gas overnight at 40° and then for 24 hours at room temperature.

The excess reagent is broken down with 2N NaOH under cooling and the reaction mixture extracted with ether. The organic phase is dried, concentrated under vacuum and chromatographed over kieselgel (eluant—toluene/ethylacetate 95:5). The title substance is isolated as an oil.

b) Hydrochloride salt

The compound from a) is converted to its hydrochloride in conventional manner e.g. by treating with 4N ethanolic HCl and melts after recrystallisation at 118°–121° C.

EXAMPLE 4

N-Methyl-N-(1-naphthylmethyl)-deca-2(trans),6(cis)-dien-4-ynyl-1-amine 1 g trans-N-Methyl-N-(1-naphthylmethyl)-6-hydroxy-dec-2-en-4-ynyl-1amine are refluxed under a water separator with 570 mg p-toluenesulphonic acid (monohydrate) in benzene. The mixture is cooled after 2 hours, the organic phase shaken a number of time with saturated aqueous $NaHCO_3$, dried and concentrated under vacuum. The residue is chromatographed over kieselgel (eluant-toluene/ethylacetate 9:1) to give the title product.

EXAMPLE 5

N-Methyl-N-(1-naphthylmethyl)-4-cyclohexyl-2-(trans)-4-pentadienyl-1-amine (A) and
N-Methyl-N-(1-naphthylmethyl)-4-cyclohexylidenyl-2-(trans)-pentenyl-1-amine (B)

1 g N-Methyl-N-(1-naphthylmethyl)-4-hydroxy-4-cyclohexyl-2-pentenyl-1-amine is refluxed under a water separator with 570 mg p-toluenesulphonic acid (monohydrate) in benzene. The mixture is cooled after 2 hours, the organic phase shaken a number of times with saturated aqueous NaHCO$_3$, dried and concentrated under vacuum. The residue is chromatographed over kieselgel (eluant-toluene/ethyl acetate 9:1) to obtain first title product (A) followed by title product (B) as oils.

EXAMPLE 6 trans-N-Methyl-N-(1-naphthylmethyl)-4-cyclohexylidenyl-2-buten-yl-amine [process e)]

3 g (1-Naphthylmethyl)amine and 2.86 g 4-cyclohexylidenyl-2-butenal are stirred in ether together with a 4 Å molecular sieve. The reaction mixture is filtered and concentrated under vacuum. The residue is taken up in methanol, treated with 800 mg NaBH$_4$ and stirred for 2 hours at room temperature.

The reaction mixture containing the secondary amine thus obtained is taken directly for reductive methylation. 8 ml 37% aqueous formaldehyde solution are added and refluxed for 1 hour. The mixture is then treated under ice-cooling with 3.6 g NaBH$_4$ and stirred for 16 hours at room temperature. The resulting mixture is concentrated under vacuum, the residue partitioned between saturated NaHCO$_3$ and ethyl acetate and the organic phase dried and concentrated. The title substance is obtained by chromatography over kieselgel (eluant—toluene/ethyl acetate 4:1) as an oil.

The following compounds of formula I can be obtained in an analogous manner.

TABLE I

| Example | R$_1$ | R$_2$ | R$_3$ | R$_4$ | R$_5$ | R$_6$ | Conf. | Physical data | Proc. |
|---|---|---|---|---|---|---|---|---|---|
| 7 | benzothiophene | H | H | CH$_3$ | H | —C≡C—(CH$_2$)$_3$—CH$_3$ | trans | oil | c, e |
| 8 | " | H | H | CH$_3$ | H | " | cis | oil | e |
| 9 | naphthyl | H | H | CH$_3$ | H | " | cis | oil | a, e |
| 10 | dihydronaphthyl | H | H | CH$_3$ | H | " | trans | oil | a, c, e |
| 11 | " | H | H | CH$_3$ | H | " | cis | oil | a, e |
| 12 | benzofuran | H | H | CH$_3$ | H | " | trans | oil | a, c, e |
| 13 | " | H | H | CH$_3$ | H | " | cis | oil | a, e |
| 14 | naphthyl | H | H | CH$_3$ | H | —C≡CH | trans | mp (hydrochloride) 150-155° | a, c, e |
| 15 | naphthyl | H | R$_3$ + R$_4$ + N (piperidine) | | H | —C≡CH | trans | mp (hydrochloride) 150-155° | a, c |
| 16 | " | H | H | CH$_3$ | H | —C≡C—C(CH$_3$)$_3$ | trans | m.p. (hydrochlor- | a, c, e |

TABLE I-continued

| Example | R₁ | R₂ | R₃ | R₄ | R₅ | R₆ | Conf. | Physical data | Proc. |
|---|---|---|---|---|---|---|---|---|---|
| | | | | | | | | ide) 199–202° (crystal inversion above 135°) | |
| 17 | " | H | H | CH₃ | H | " | cis | oil | a, e |
| 18 | " | H | H | CH₃ | H | —C≡C—C₆H₅ | trans | oil | a, c, e |
| 19 | " | H | H | CH₃ | H | " | cis | oil | a, e |
| 20 | " | H | H | CH₃ | H | —C≡C—CH(CH₃)(C₂H₅) | trans | m.p. (hydrochloride) 160–162° | a, c, e |
| 21 | " | H | H | CH₃ | H | " | cis | oil | a, e |
| 22 | " | H | H | CH₃ | H | —C≡C—CH₂—CH(CH₃)₂ | trans | m.p. (hydrochloride) 124–126° | a, c, e |
| 23 | " | H | H | CH₃ | H | " | cis | oil | a, e |
| 24 | " | H | H | CH₃ | H | —C≡C—(2-thienyl) | trans | oil | a, c, e |
| 25 | 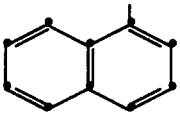 | H | H | CH₃ | H | —C≡C—C(OH)(CH₃)₂ | trans | oil | c, e |
| 26 | " | H | H | CH₃ | H | —C≡C—C(OH)(C₂H₅)₂ | trans | oil | b, c, e |
| 27 | " | H | H | CH₃ | H | —C≡C—CH(OH)—(CH₂)₃—CH₃ | trans | oil | b, c, e |
| 28 | " | H | H | CH₃ | H | —C≡C—C(OH)(CH₃)(C₂H₅) | trans | oil | b, c, e |
| 29 | " | H | H | CH₃ | H | —C=C—C(OH)(CH₃)(C(CH₃)₃) | trans | oil | b, c, e |
| 30 | " | H | H | CH₃ | H | —C≡C—(CH₂)₃—CH₃ | trans | mp (hydrochloride) 118–121° | a, e |
| 31 | " | H | H | CH₃ | H | —C≡C—(CH₂)₂—CH₃ | trans | oil | a, c, e |
| 32 | " | H | H | CH₃ | H | —C≡C—(CH₂)₄—CH₃ | trans | oil | a, c, e |
| 33 | " | H | H | CH₃ | H | —C≡C—(CH₂)₅—CH₃ | trans | oil | a, c, e |
| 34 | " | H | R₃ + R₄ + N 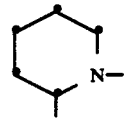 | | H | —C≡C—(CH₂)₂—CH₃ | trans | oil | a, c |
| 35 | " | H | " | | H | —C≡C—(CH₂)₃—CH₃ | trans | oil | a, c |
| 36 | 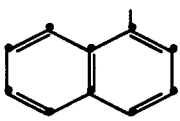 | H | H | CH₃ | H | —C≡C—CH=CH—(CH₂)₂—CH₃ | trans | oil | a, c, e |

TABLE I-continued

| Example | R₁ | R₂ | R₃ | R₄ | R₅ | R₆ | Conf. | Physical data | Proc. |
|---|---|---|---|---|---|---|---|---|---|
| 37 | " | H | H | CH₃ | H | —C≡C—C(C₂H₅)=CH.CH₃ | trans | oil | a, c, d, e |
| 38 | " | H | H | CH₃ | H | —C≡C—C(CH₃)=CH.CH₃ | trans | oil | a, c, d, e |
| 39 | " | H | H | CH₃ | H | —C≡C—C(C(CH₃)₃)=CH₂ | trans | oil | a, c, d, e |
| 40 | " | H | H | CH₃ | H | —C(C₆H₅)=CH₂ | trans | oil | c, d, e |
| 41 | " | H | H | CH₃ | H | —C(CH₂CH(CH₃)CH₃)=CH₂ | trans | oil | c, d, e |
| 42 | " | H | H | CH₃ | H | —C((CH₂)₃—CH₃)=CH₂ | trans | oil | c, d, e |
| 43 | " | H | H | CH₃ | H | —C(C(CH₃)₃)=CH₂ | trans | oil | c, d, e |
| 44 | 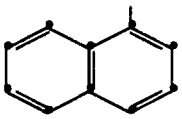 | H | H | CH₃ | H | { —C(CH₃)=CH-C₆H₅ ; —C(CH₃)=CH-C₆H₅ } 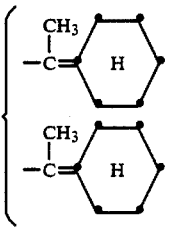 | trans oil / trans oil | oil | c, e |
| 45 | " | H | H | CH₃ | H | —CH=CH-C₆H₅ 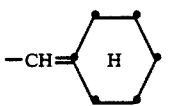 | trans | oil | c, d |
| 46 | " | H | H | CH₃ | H | —C≡C—CH₂OH | trans | oil | b, c, e |
| 47 | " | H | H | CH₃ | CH₃ | —C≡C—(CH₂)₃—CH₃ | trans | oil | a, c, e |
| 48 | " | H | H | CH₃ | CH₃ | " | cis | oil | a, e |
| 49 | " | H | H | CH₃ | H | —C≡C—C(CH₃)(CH₃)—C₂H₅ | trans | oil | a, c, e |
| 50 | " | H | H | CH₃ | H | " | cis | oil | a, e |
| 51 | " | H | H | CH₃ | H | —C≡C—(cyclopentenyl) 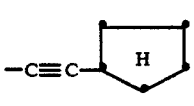 | trans | oil | a, c, e |
| 52 | 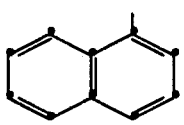 | H | H | CH₃ | H | —C≡C—(cyclopentenyl) 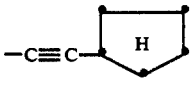 | cis | oil | a, e |

TABLE I-continued

| Example | R1 | R2 | R3 | R4 | R5 | R6 | Conf. | Physical data | Proc. |
|---|---|---|---|---|---|---|---|---|---|
| 53 | " | H | H | CH3 | H | 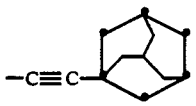 | trans | oil | a, c, e |
| 54 | " | H | H | CH3 | H | " | cis | oil | a, e |
| 55 | 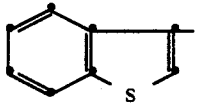 | H | H | CH3 | H | 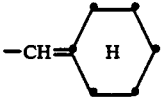 | trans | oil | c, d, e |
| 56 | 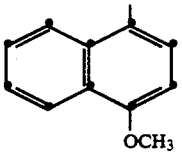 | H | H | CH3 | H | —C≡C—C(CH3)3 | cis | oil | a, c, e |
| 57 | 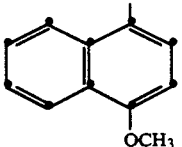 | H | H | CH3 | H | —C≡C—C(CH3)3 | cis | oil | a, e |
| 58 | R1 + R2 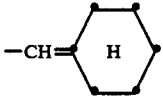 | | H | CH3 | H | —CH= | trans | oil | c, d, e |
| 59 | " | H | H | CH3 | H | —C≡C—C(CH3)3 | trans | oil | a, c, e |

In the following table NMR data are given. Data comprises peaks in ppm relative to TMS as standard in CDCL3. Types of peaks are
- m = multiplet
- dt = double triplet
- dm = double multiplet
- s = singlet
- d = doublet
- t = triplet
- ps.t = pseudo triplet
- dd = double doublet
- dbr = double broad
- br = broad
- qua = quartet
- mbr = multiple broad
- sext = sextuplet
- ddd = double double doublet
- sbr = single broad

| Example | Isomer | Spectrum |
|---|---|---|
| 1, 7 | trans | δ = 7.7–8.0(m, 2H); 7.15–7.45(m, 4H); 6.14(dt, J=16 and 2 × 6.5 Hz, 1 olef. H); 6.65(dm, J=16 Hz, 1 olef. H); 3.72 (s, 2H); 3.10(d, J=6.5 Hz, 2H); 2.3 (m, 2H); 2.24(s, 3H); 1.2–1.7(m, 4H); 0.9(ps.t., 3H). |
| 1, 8 | cis | δ = 7.7–8.0(m, 2H); 7.15–7.45(m, 4H); 6.0(dt, J=11 and 2 × 6.5 Hz, 1 olef. H); 5.64(dm, J=11 Hz, 1 olef. H); 3.66 (s, 2H); 3.35(d, J=6.5 Hz, 2H); 2.34 (m, 2H); 2.28(s, 3H); 1.2–1.7(m, 4H); 0.9(ps.t., 3H). |
| 9 | cis | δ = 8.2–8.4(m, 1H); 7.7–7.9(m, 2H); 7.3–7.6(m, 4H); 6.05(dt, J=10.8 + 2 × 7 Hz, 1 olef. H); 5.65(dm, J=10.8 Hz, 1 olef H); 3.92(s, 2H); 3.38(dd, J=7 u. 1.5 Hz, 2H); 2.34(m, 2H); 2.25(s, 3H); 1.2–1.8 (m, 4H); 0.94(m, 3H). |
| 10 | trans | δ = 6.9–7.2(m, 3H); 6.12(dt, J=16 and 2 × 6.5 Hz, 1 olef. H); 5.64(dm, J=16 Hz, 1 olef. H); 3.4(s, 2H); 3.05(d, J=6.5 Hz, 2H); 2.7–2.9(m, 4H); 2.2–2.4(m, 2H); 2.18(s, 3H); 1.65–1.9(m, 4H); 1.3–1.7 (m, 4H); 0.92(m, 3H). |
| 11 | cis | δ = 6.85–7.2(m, 3H); 5.97(dt, J=11 and 6.5 Hz, 1 olef. H); 5.60(dm, J=11 Hz, 1 olef. H); 3.45(s, 2H); 3.30(d, J=6.5 Hz, 2H); 2.7–2.9(m, 4H); 2.2–2.4(m, 2H); 2.22(s, 3H); 1.7–1.9(m, 4H); 1.3–1.7 (m, 4H); 0.95(m, 3H). |
| 12 | trans | δ = 7.1–7.8(m, 5H); 6.14(dt, J=16 and 2 × 6.5 Hz, 1 olef. H); 5.65(dm, J= 16 Hz, 1 olef. H); 3.63(s, 2H); 3.1 (d, J=6.5 Hz, 2H); 2.2–2.4(m, 2H); 2.25(s, 3H); 1.2–1.7(m, 4H); 0.9(m, 3H). |
| 13 | cis | δ = 7.1–7.8(m, 5H); 6.0(dt, J=11 and 2 × 6.5 Hz, 1 olef. H); 5.64(dm, J= 11 Hz, 1 olef. H); 3.66(s, 2H); 3.35 (d, J=6.5 Hz, 2H); 2.2–2.4(m, 2H); 2.30(s, 3H); 1.2–1.7(m, 4H); 0.9(m, 3H). |
| 16 | trans | δ = 8.2–8.35(m, 1H); 7.7–7.9(m, 2H); 7.3– |

-continued

| Example | Isomer | Spectrum |
|---|---|---|
| | | 7.6(m, 4H); 6.18(dt, J=17 and 2 × 7 Hz); 5.65 (dm, J=17 Hz, 1H); 3.9(s, 2H); 3.12(dd, J=7 u. 1 Hz, 2H); 2.22(s, 3H); 1.25(s, 9H). |
| 17 | cis | δ = 8.2–8.35(m, 1H); 7.7–7.9(m, 2H); 7.3–7.6(m, 4H); 6.03(dt, J=11 and 2 × 6.5 Hz, 1H); 5.65(dbr, J=11 Hz, 1H); 3.92(s, 2H); 3.38(d, J=6.5Hz, 2H); 2.26(s, 3H); 1.27(s, 9H). |
| 18 | trans | δ = 8.2–8.35(m, 1H); 7.7–7.9(m, 2H); 7.2–7.6(m, 9H); 6.36(dt, J=16 and 2 × 6.5 Hz, 1H); 5.9(dm, J=16 Hz, 1H); 3.94(s, 2H); 3.22(d, J=6.5 Hz, 2H); 2.28(s, 3H). |
| 19 | cis | δ = 8.2–8.4(m, 1H); 7.7–7.9(m, 2H); 7.2–7.6(m, 9H); 6.20(dt, J=11 and 2 6.5 Hz, 1H); 5.85(d, J=11 Hz, 1H); 3.98(s, 2H); 3.50(d, J=6.5 Hz, 2H); 2.30(s, 3H). |
| 20 | trans | δ = 8.2–8.4(m, 1H); 7.7–7.9(m, 2H); 7.3–7.6(m, 4H); 6.20(dt, J=16 and 2 × 6.5 Hz, 1H); 5.80(dm, J=16 Hz, 1H); 3.90(s, 2H); 3.14(d, J=6.5 Hz, 2H); 2.5(m, 1H); 2.24(s, 3H); 1.2–1.7 (m, 2H); 1.18(d, J=7 Hz, 3H); 1.0(t, J=7 Hz, 3H). |
| 21 | cis | δ = 8.2–8.4(m, 1H); 7.7–7.9(m, 2H); 7.3–7.6(m, 4H); 6.05(dt, J=11 and 2 × 6.5 Hz, 1H); 5.67(dm, J=11 Hz, 1H); 3.94(s, 2H); 3.40(d, J=6.5 Hz, 2H); 2.55(m, 1H); 2.28(s, 3H); 1.2–1.8 (m, 2H); 1.20(d, J=7 Hz, 3H); 1.02 (t, J=7 Hz, 3H). |
| 22 | trans | δ = 8.2–8.35(m, 1H); 7.65–7.9(m, 2H); 7.3–7.6(m, 4H); 6.20(dt, J=16 and 2 × 6.5 Hz, 1H); 5.68(dm, J=16 Hz, 1H); 3.88(s, 2H); 3.13(d, J=6.5Hz, 2H); 2.22(s, 3H); 2.2(m, 2H); 1.6–2.1 (m, 1H); 1.0(d, J=7 Hz, 6H). |
| 23 | cis | δ = 8.2–8.4(m, 1H); 7.7–7.9(m, 2H); 7.3–7.6(m, 4H); 6.04(dt, J=12 and 2 × 7 Hz, 1H); 5.65(dbr, J=12 Hz, 1H); 3.90(s, 2H); 3.38(d, J=7 Hz, 2H); 2.24 (s, 3H); 2.2(m, 2H); 1.6–2.0(m, 1H); 1.0(d, J=7 Hz, 6H). |
| 24 | trans | δ = 8.2–8.4(m, 1H); 7.65–7.9(m, 2H); 7.3–7.6(m, 4H); 7.15–7.3(m, 2H); 6.95 (m, 1H); 6.36(dt, J=16 u. 2 × 6 Hz, 1H); 5.9(dbr, J=16 Hz, 1H); 3.92(s, 2H); 3.20(d, J=6 Hz, 2H); 2.28(s, 3H). |
| 2, 25 | trans | δ = 8.15–8.35(m, 1H); 7.6–7.9(m, 2H); 7.3–7.6(m, 4H); 6.22(dt, J=16 and 2 × 6.5 Hz, 1H); 5.67(dt, J=16 and 2 × 1.5 Hz, 1H); 3.88(s, 2H); 3.13(dd, J=6.5 u. 1.5 Hz, 2H); 2.22(s, 3H); 2.15(br. —OH); 1.5(s, 6H). |
| 26 | trans | identical with Ex. 2, 25 except δ = 1.8(br, OH); 1.65(qua, J=8 Hz, 4H); 1.0(t, J=8 Hz, 6H). |
| 27 | trans | δ = 8.2–8.35(m, 1H); 7.6–7.9(m, 2H); 7.3–7.6(m, 4H); 6.26(dt, J=16 and 2 × 6 Hz, 1H); 5.7(dm, J=16 Hz, 1H); 4.46 (mbr, 1H); 3.90(s, 2H); 3.15(d, J=6 Hz, 2H); 2.25(s, 3H); 2.0(br, OH); 1.2–1.8(m, 6H); 0.9(m, 3H). |
| 28 | trans | δ = 8.15–8.35(m, 1H); 7.7–7.9(m, 2H); 7.3–7.6(m, 4H); 6.25(dt, J=16 and 2 × 6.5 Hz, 1 olef. H); 5.70(dbr, J=16 Hz, 1H); 3.9(s, 2H); 3.14(d, J=6.5 Hz, 2H); 2.24(s, 3H); 2.1(br, OH); 1.72(qua, J=7 Hz, 2H); 1.50(s, 3H); 1.04(t, J=7 Hz, 3H). |
| 29 | trans | δ = 8.15–8.35(m, 1H); 7.7–7.9(m, 2H); 7.3–7.6(m, 4H); 6.22(dt, J=16 and 2 × 6.5 Hz, 1H); 5.70(dm, J=16 Hz, 1H); 3.9(s, 2H); 3.14(d, J=6.5 Hz, 2H); 2.24(s, 3H); 1.95(m, OH); 1.45(s, 3H); 1.06(s, 9H). |
| 3, 30 | trans | δ = 8.2–8.35(1 arom. H); 7.7–7.9(2 arom. H); 7.3–7.6(4 arom. H); 6.17 (dt, 1 olef. H, J=16 + 2 × 6.5 Hz); 5.67(d, 1 olef. H, J=16 Hz); 3.89(s, |

-continued

| Example | Isomer | Spectrum |
|---|---|---|
| | | 2H); 3.13(d, 2H, J=6.5Hz); 2.21(s, 3H); 2.2–2.4(m, 2H); 1.2–1.8(4H); 0.8–1.05 (m, 3H). |
| 31 | trans | identical with Ex. 3, 30 except: δ = 2.28(t, 2H); 1.55(sext., 2H); 1.0(t, 3H). |
| 32 | trans | identical with Ex. 3, 30 except: δ = 1.2–1.8(m, 6H). |
| 33 | trans | identical with Ex. 3, 30 except: δ = 1.2–1.8(m, 8H). |
| 34 | trans | δ = 8.5(br, 1H); 7.3–7.9(m, 6H); 6.02 (ddd, J=5, 8 + 16 Hz, 1H); 5.46(dbr, J=16 Hz, 1H); 3.80(br, 1H); 3.1–3.35 (m, 2H); 2.52(dd, 8 + 14 Hz, 1H); 2.0–2.35(m, 3H); 1.6–2.0(m, 6H); 1.54 (sext., J=7 Hz, 2H); 0.97(t, J=7 Hz, 3H). |
| 35 | trans | identical with Ex. 34 except: δ = 1.3–1.7(m, 4H); 0.9(ps.t, 3H). |
| 4, 36 | trans | δ = 8.2–8.35(m, 1H); 7.7–7.9(m, 2H); 7.3–7.6(m, 4H); 6.26(dt, J=15.5 + 2 × 6.5 Hz, 1H); 5.9(dt, J=11 + 2 × 7 Hz); 5.85(d, J=15.5 Hz, 1H); 5.58(dbr, J=11 Hz); 3.92(s, 2H); 3.18(d, J=6.5 Hz, 2H); 2.35(t, 2H); 2.26(s, 3H); 1.2–1.7 (m, 2H); 0.95(ps.t, 3H). |
| 37 | trans | δ = 8.15–8.35(m, 1H); 7.7–7.9(m, 2H); 7.3–7.6(m, 4H); 6.25(dt, J=16 + 6 Hz, 1H); 5.86(d, J=16 Hz, 1H); 5.70(t, J=7 Hz, 1H); 3.94(s, 2H); 3.20(d, J=6 Hz, 2H); 2.26(s, 3H); 2.16(qua, J=8 Hz, 2H); [1.8(d, J=7 Hz) and 1.7(d, J=7 Hz); Σ 3H, in ratio 6/1]; 1.06(t, 3H). |
| 38 | trans | δ = 8.2–8.35(m, 1H); 7.7–7.9(m, 2H); 7.3–7.6(m, 4H); 6.30(dt, J=16 + 2 × 6 Hz, 1H); 5.86(d, J=16 Hz, 1H); 5.75(m, 1H); 3.93(s, 2H); 3.18(d, J=6 Hz, 2H); 2.26 (s, 3H); 1.87(s, 3H); 1.8 u. 1.7(2 d, 3H). |
| 39 | trans | δ = 8.2–8.4(m, 1H); 7.7–7.9(m, 2H); 7.3–7.6(m, 4H); 6.28(dt, J=16 + 2 × 6.5 Hz, 1H); 5.84(dm, J=16 Hz, 1H); 5.30(m, 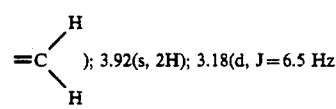 ); 3.92(s, 2H); 3.18(d, J=6.5 Hz, 2H); 2.26(s, 3H); 1.18(s, 9H). |
| 5, 44 A | trans | δ = 8.2–8.35(1 arom. H); 7.7–7.9(2 arom. H); 7.3–7.6(4 arom. H); 6.22(d, 1 olef. H, J=16 Hz); 5.93(dt, 1 olef. H, J=16 + 2 × 6.5 Hz); 4.87 u. 4.83 (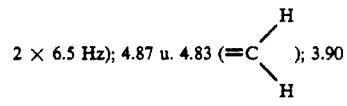); 3.90 (s, 2H); 3.19(d, 2H, J=6.5 Hz); 2.25 (s, 3H); 1.0–2.4(11 H, Cyclohexyl). |
| B | trans | δ = 8.2–8.35(1 arom. H); 7.7–7.9(2 arom. H); 7.3–7.6(4 arom. H); 6.79(d, 1 olef. H, J=16 Hz); 5.80(dt, 1 olef. H, J=16 + 2 × 6.5 Hz); 3.92(s, 2H); 3.24(d, 2H, J=6.5 Hz,); 2.2–2.5(m, 4H); 2.26(s, 3H); 1.88(s, 3H), 1.58(br, 6H). |
| 40 | trans | δ = 8.15–8.30(m, 1H); 7.7–7.9(m, 2H); 7.3–7.6(m, 9H); 6.51(d, J=18 Hz, 1H); 5.82(dt, J=18 + 2 × 7.5 Hz, 1H); [5.26(sbr, 1H) + 5.14(d, J=2 Hz, 1H) 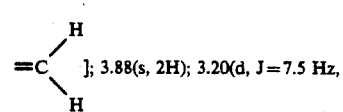 ]; 3.88(s, 2H); 3.20(d, J=7.5 Hz, 2H); 2.22(s, 3H). |
| 41 | trans | δ = 8.2–8.35(m, 1H); 7.7–7.9(m, 2H); 7.3–7.6(m, 4H); 6.24(dt, J=16 Hz, 1 olef. H); 5.85(dt, J=16 + 2 × 6.5 Hz, 1 olef. |

-continued

| Example | Isomer | Spectrum |
|---|---|---|
| | | H); 4.95(dd, J=11 + 2 Hz, 2 olef. H); 3.9(s, 2H); 3.18(d, J=6.5 H, 2H); 2.24 (s, 2H); 2.13(d, J=6.5 Hz, 2H); 1.6–2.1 (m, 1H); 0.9(d, J=6.5 Hz, 6H). |
| 42 | trans | δ = 8.2–8.35(m, 1H); 7.65–7.9(m, 2H); 7.3–7.6(m, 4H); 6.26(d, J=16 Hz, 1H); 5.86(dt, J=16 + 2 × 6.5 Hz, 1H); 4.95 (s, =C⟨H/H⟩); 3.90(s, 2H); 3.18(d, J=6.5 Hz, 2H); 2.24(s, 3H); 2.15–2.35(m, 2H); 1.1–1.7(m, 4H); 0.9(ps.t, 3H). |
| 43 | trans | δ = 8.2–8.35(m, 1H); 7.7–7.9(m, 2H); 7.3–7.6(m, 4H); 6.30(d, J=15.5 Hz, 1H); 6.02(dt, J=15.5 Hz + 2 × 6.5 Hz, 1H); [5.07(sbr, 1H) + 4.80(d, J=2 Hz, 1H), =C⟨H/H⟩]; 3.9(s, 2H); 3.16(d, 2H); 2.25 (s, 3H); 1.1(s, 9H). |
| 6, 45 | trans | δ = 8.2–8.35(1 arom. H); 7.7–7.9(2 arom. H); 7.3–7.6(4 arom. H); 6.52(dd, 1 olef. H, J=15 u. 10 Hz); 5.86(d, 1 olef. H, J=10 Hz); 5.79(dt, 1 olef, H, J=15 + 2 × 6.5 Hz); 3.92(s, 2H); 3.20(d, J=6.5 Hz, 2H); 2.25(s, 3H); 2.1–2.4(m, 4H); 1.6(br, 6H). |
| 46 | trans | δ = 8.15–8.35(m, 1H); 7.7–7.9(m, 2H); 7.3–7.6(m, 4H); 6.3(dt, J=16 + 2 × 6.5 Hz, 1); 5.7(dm, J=16 Hz, 1H); 4.34(d, J=2 Hz, 2H); 3.9(s, 2H); 3.16(d, J=6.5 Hz, 2H); 2.24(s, 3H); 2.2(OH). |
| 47 | trans | δ = 8.2–8.35(m, 1H); 7.65–7.9(m, 2H); 7.3–7.5(m, 4H); 6.17(dd, J=16 + 7 Hz, 1H); 5.58(dm, J=16 Hz, 1H); 3.9(AB-System, 2H); 3.25(m, 1H); 2.1–2.3(m, 2H); 2.14(s, 3H); 1.3–1.6(m, 4H); 1.18(d, J=7 Hz, 3H); 0.85(m, 3H). |
| 48 | cis | δ = 8.2–8.35(m, 1H); 7.6–7.9(m, 2H); 7.3–7.6(m, 4H); 5.93(dd, J=11 + 9 Hz, 1H); 5.6(dm, J=11 Hz, 1H); 3.96(AB-System, 2H); 3.8(m, 1H); 2.1–2.3(m, 2H); 2.16(s, 3H); 1.2–1.6(m, 4H); 1.26(d, J=7 Hz, 3H); 0,82(m, 3H). |
| 49 | trans | δ = 8.15–8.35(m, 1H); 7.6–7.9(m, 2H); 7.3–7.6(m, 4H); 6.14(dt, J=16 + 2 × 6.5 Hz, 1H); 5.66(dm, J=16 Hz, 1H); 3.86(s, 2H); 3.10(d, J=6.5 Hz, 2H); 2.2(s, 3H); 1.4(qua, J=7 Hz, 2H); 1.15(s, 6H); 0.9(t, J=7 Hz, 3H). |
| 50 | cis | δ = 8.2–8.35(m, 1H); 7.6–7.9(m, 2H); 7.3–7.6(m, 4H); 6.0(dt, J=11 + 2 × 6.5 Hz, 1H); 5.64(dm, J=11 Hz, 1H); 3.9(s, 2H); 3.35(d, J=6.5 Hz, 2H); 2.22(s, 3H); 1.45 (qua, J=7 Hz, 2H); 1.18(s, 6H); 0.95(t, J=7 Hz, 3H). |
| 51 | trans | δ = 8.15–8.35(m, 1H); 7.6–7.9(m, 2H); 7.3–7.6(m, 4H); 6.16(dt, J=16 + 2 × 6.5 Hz, 1H); 5.66(dm, J=16 Hz, 1H); 3.86(s, 2H); 3.10(d, J=6.5 Hz, 2H); 2.7(br, 1H); 2.2(s, 3H); 1.4–2.1(m, 8H). |
| 52 | cis | δ = 8.15–8.35(m, 1H); 7.6–7.9(m, 2H); 7.3–7.6(m, 4H); 6.0(dt, J=11 + 2 × 6.5 Hz, 1H); 5.64(dm, J=11 Hz, 1H); 3.9(s, 2H); 3.36(d, J=6.5 Hz, 2H); 2.75(br, 1H); 2.22(s, 3H); 1.4–2.1(m, 8H). |
| 55 | trans | δ = 7.8–8.1(m, 2H); 7.25–7.5(m, 3H); 6.50(dd, J=17 + 12 Hz, 1H); 5.85(d, J=12 Hz, 1H); 5.74(dt, J=17 u. 2 × 7 Hz, 1H); 3.77(s, 2H); 3.14(d, J=7 Hz, 2H); 2.0–2.4(m, 4H); 2.25(s, 3H); 1.55(sbr, 6H). |
| 56 | trans | δ = 8.2–8.4(m, 2H); 7.25–7.7(m, 3H); 6.74(d, J=8 Hz, 1H); 6.2(dt, J=18 + 2 × 7 Hz, 1H); 5.67(dt, J=18 u. 2 × 15 Hz, 1H); 4.0(s, 3H); 3.82(s, 2H); 3.10(dd, J=7 u. 1.5 Hz); 2.2 (s, 3H); 1.24(s, 9H). |
| 57 | cis | δ = 8.2–8.4(m, 2H); 7.25–7.7(m, 3H); 6.74(d, J=8 Hz, 1H); 6.05(dt, J=12 + 2 × 7.5 Hz, 1H); 5.65(dt, J=12 u. 2 × 1.5 Hz, 1H); 4.0(s, 3H); 3.85(s, 2H); 3.35(dd, J=7.5 u. 1.5 Hz, 2H); 2.24(s, 3H); 1.26(s, 9H). |
| 58 | trans | δ = 7.2–7.8(m, 6H); 6.44(dd, J=17 + 12 Hz, 1H); 5.80(d, J=12 Hz, 1H); 5.66(dt, J=17 + 2 × 7 Hz, 1H); 5.0(t, J=6 Hz, 1H); 3.33(d, J=6 Hz, 2H); 3.14(d, J=7 Hz, 2H); 2.0–2.4(m, 4H); 2.12(s, 3H); 1.5(sbr, 6H). |
| 59 | trans | δ = 7.1–7.7(m, 6H); 6.04(dt, J=16 + 2 × 6.5 Hz, 1H); 5.6(dm, J=16 Hz, 1H); 4.9(t, J=6 Hz, 1H); 3.22(d, J=6 Hz, 2H); 3.0(d, J=6.5 Hz, 2H); 2.1(s, 3H); 1.18(s, 9H). |
| 53 | trans | δ = 8.15–8.35(m, 1H); 7.6–7.9(m, 2H); 7.3–7.6(m, 4H); 6,15(dt, J=16 + 2 × 6.5 Hz, 1H); 5.65(dm, J=16 Hz, 1H); 3.85(s, 2H); 3.10(d, J=6.5 Hz, 2H); 2.2(s, 3H); 1.8–2.1(br, 9H); 1.6–1.8(br, 6H). |

The required starting materials can be obtained e.g. as follows.

1. COMPOUNDS OF FORMULA IV

A) (3-Benzo[b]thiophenemethyl)methylamine (for Ex. 1)

3-Chloromethylbenzo[b]thiophene is dissolved in benzene, added dropwise to a ca. 10-fold excess of methylamine in ethanol at 0°–5° and then stirred for 16 hours at room temperature. The crude mixture is concentrated under vacuum, the residue partitioned between methylenechloride and 1N NaOH and the organic phase dried and evaporated under vacuum. The purified product is obtained by vacuum distillation b.p. 90°–94°/1,33 Pa.

B) (3-Benzo[b]furanmethyl)methylamine (for Ex. 12 and 13)

Obtained analogously to Example A) b.p. 105°–110°/5.3 Pa.

C) 2-(1-Naphthyl)piperidine (for Ex. 15, 34 and 35)

A Grignard complex is prepared by adding 43.4 g of 1-bromonaphthalene in absolute ether dropwise to 5.1 g of magnesium in 50 ml of absolute ether. The ether is removed from the reaction mixture and replaced by absolute benzene. 8 g 6-Methoxy-2,3,4,5-tetrahydropyridine are added to the boiling reaction mixture. After a further 8 hours the mixture is cooled, treated with saturated aqueous ammoniumchloride solution and the reaction product removed from the organic phase by shanking with aqueous HCl-solution. After neutralisation and working up the 2-(1-naphthyl)-3,4,5,6-tetrahydropyridine is dissolved directly in methanol and reduced with NaBH₄. After normal working up the product is converted with alcoholic HCl solution to its hydrochloride. M.p. 287°–289° (after intensive drying under high vacuum 328°–329°).

2. COMPOUNDS OF FORMULA V

D) 1-Bromo-6,6-dimethyl-2-hepten-4-yne (for Ex. 16, 17, 56, 57 and 59)

a) 6,6-Dimethyl-1-hepten-4-yn-3-ole 38 ml 3,3-Dimethyl-1-butyne are dissolved in abs. tetrahydrofuran and 172 ml of a 20% solution of n-butyl-lithium added dropwise under protective gas at a temperature of −20°. The reaction mixture is then cooled to −75° and 19.3 g acrolein in 20 ml of tetrahydrofuran added dropwise. The mixture is warmed to room temperature, reacted with saturated aqueous NH₄Cl and extracted a number of times with ether. The organic phase is dried, concentrated and the purified product obtained by vacuum distillation, b.p. 70°–72°/1600 Pa.

b) 1-Bromo-6,6-dimethyl-2-hepten-4-yne 50 ml 48% HBr and 10 g PBr₃ are stirred at 40° until a homogenous mixture is obtained. An alcoholic solution of 13.5 g 6,6-dimethyl-1-hepten-4-yn-3-ole are added dropwise at 10° and stirred for 1¼ hours at room temperature. The reaction mixture is poured onto ice and extracted a number of times with hexane. The organic phase is washed a number of times with aqueous NaCl, dried and concentrated. NMR-spectography shows that the oily product comprises a 3:1 mixture of trans- and cis-1-bromo-6,6-dimethyl-2-hepten-4-yne and is taken directly for alkylation.

NMR: δ=5.5–6.4 (m, 2 olef. H), [4.15 (d. J=8Hz) and 3.95 (d, J=8Hz) in ratio 1:3, 2H,=CH—C$\underline{H_2}$Br], 1.20 (m, 9H).

Analogously to D) above the following compounds of formula V can be obtained.

TABLE II a) $R_5$—CH=CH—$\overset{\text{OH}}{\underset{|}{\text{CH}}}$—C≡C—$R_{11}$ b) A—CH—CH=CH—C≡C—$R_{11}$
       |
       $R_5$

| | $R_{11}$ | $R_5$ | A | Physical data | for Ex. |
|---|---|---|---|---|---|
| E) a b | —CH(CH₃)(C₂H₅) | H | Br̄ | b.p. 75–80°/1460 Pa oil | 20, 21 |
| F) a b | —CH₂.CH(CH₃)(CH₃) | H | Br̄ | b.p. 87–91°/1730 Pa oil | 22, 23 |
| G) a b | —C(CH₃)(C₂H₅)(CH₃) | H | Br̄ | b.p. 90°/1460 Pa oil | 49, 50 |
| H) a b | (cyclopropyl) | H | Br̄ | b.p. 94–96°/800 Pa oil | 51, 52 |
| I) a b | —(CH₂)₃—CH₃ | CH₃ | Br̄ | b.p. 92–93°/530 Pa oil | 47, 48 |

The remaining compounds of formula V can be obtained analogously to D) above.

3. COMPOUNDS OF FORMULA VIII

M)
N-Methyl-N-(1-naphthylmethyl)octa-2,4-diynyl-1-amine (for Ex. 31)

9 g 1,3-Heptadiyne, 16 g methyl-(1-naphthylmethyl)amine, 2.8 g paraformaldehyde and 1.3 g ZnCl₂ (anhydrous) are heated for 3 hours at 100° in absolute dioxane. After cooling the solvent is removed under vacuum, the residue partitioned between chloroform and aqueous NaHCO₃-solution and the organic phase dried and concentrated. The purified product is obtained by chromatography over kieselgel (toluene/ethyl acetate 9:1) as an oil.

N)
N-Methyl-N-(1-naphthylmethyl)-2,4-nonadiynyl-1-amine (for Ex. 3)

8.25 g 1-Bromohexyne are added dropwise to a mixture of 16 g N-methyl-N-(1-naphthylmethyl)-propargylamine, 0.5 g NH₂OH.HCl, 0.25 g CuCl and 20 ml 70% ethylamine. The reaction mixture is stirred overnight at room temperature, treated with an aqueous solution of 1 g KCN and extracted a number of times with ether. The organic phase is washed with saturated aqueous NaCl, dried and evaporated. The title substance is obtained as an oil after chromatography over Kieselgel (eluant toluene/ethyl acetate 95:5).

O)
N-Methyl-N-(1-naphthylmethyl)-4-t.butyl-pent-2-yn-4-enyl-1-amine (for Ex. 43)

933 mg N-Methyl-N-(1-naphthylmethyl)-4-hydroxy-4,5,5-trimethyl-2-hexynyl-1-amine are dissolved in abs. pyridine, warmed to 50° and 0.4 ml POCl₃ added. Stirring is carried out for one hour at 90°, the mixture poured onto ice and the reaction product isolated as an oil by extraction with ether and chromatography over kieselgel (eluant toluene/ethyl acetate 9:1).

Analogously to M), N) and O) above, the following compounds of formula VIII may be obtained.

TABLE III (1-naphthyl)—CH($R_3$)—N($R_4$)—C≡C—$R_6$

| | $R_3$ | $R_4$ | $R_6$ | Physical data | For Ex. |
|---|---|---|---|---|---|
| P) | H | CH₃ | —C≡C—(CH₂)₄—CH₃ | oil | 32 |
| Q) | H | CH₃ | —C≡C—(CH₂)₅—CH₃ | oil | 33 |
| R) | H | CH₃ | —C≡C—C(CH₃)₃ | oil | 16 |
| S) | $R_3$ + $R_4$ + N | | —C≡C—(CH₂)₂—CH₃ | oil | 34 |
| T) | (piperidinyl) | | —C≡C—(CH₂)₃—CH₃ | oil | 35 |

The remaining compounds of formula VIII can be prepared analogously to M), N) and O) above.

4. COMPOUNDS OF FORMULA IF

U)
N-Methyl-N-(1-naphthylmethyl)-4-hydroxy-4-cyclohexyl-2-pentenyl-1-amine (for Ex. 5)

a) N-Methyl-N-(1-naphthylmethyl)-4-hydroxy-4-cyclohexylpent-2-ynyl-1-amine 10.7 ml of a 15% solution of BuLi in hexane are added dropwise to 3 g N-methyl-N-(1-naphthylmethyl)propargyl amine in absolute tetrahydrofuran and after 30 minutes reacted with a solution of 1.79 g cyclohexyl-methyl ketone. Stirring is continued for 24 hours at room temperature and the mixture poured onto ice and extracted with ether. The organic phase is washed, dried and concentrated under vacuum. Chromatography over kieselgel (eluant toluene/ethylacetate 4:1) yields the title product as an oil.

b) N-Methyl-N-(1-naphthylmethyl)-4-hydroxy-4-cyclohexyl-2-pentenyl-1-amine 10 g of the substance obtained under a) are dissolved in tetrahydrofuran and added dropwise to a suspension of 1.4 g LiAlH₄ in abs. tetrahydrofuran and the mixture refluxed for 3 hours. Excess reagent is destroyed with ethyl acetate/H₂O. After extraction with ether, drying and evaporation under vacuum followed by chromatography over kieselgel (eluant $CHCl_3/C_2H_5OH$ 95:5) the title product is obtained as an oil.

Analogously to U) above the following compounds can be obtained.

TABLE IV

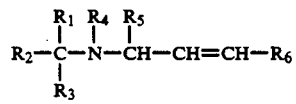

| $R_x$ | physical data [a) and b)] | For Ex. |
|---|---|---|
| V) a) b) } —CH₂—CH(CH₃)CH₃ | oil | 41 |
| W) a) b) } —(CH₂)₃—CH₃ | oil | 42 |
| X) a) b) } —C(CH₃)₃ | oil | 43 |
| Y) a) b) } —C₆H₅ | oil | 40 |

Compounds of formula IX can be prepared analogously to Example 6 above and are preferably taken directly without further purification or isolation for the final step.

| Example | Spectrum |
|---|---|
| N | δ = 8.2–8.35 (1 arom. H); 7.7–7.9 (2 arom. H); 7.3–7.6 (4 arom. H); 3.97 (s, 2H); 3.37 (s, 2H) 2.40 (s, 3H); 2.2–2.4 (m, 2H); 1.2–1.8 (4H); 0.8–1.05 (m, 3H). |
| M | identical with N except: δ = 2.28 (t, 2H); 1.58 (sext., 2H); 1.0 (t, 3H) |
| P | identical with N except: δ = 1.2–1.8 (m, 6H). |
| Q | identical with N except: δ = 1.2–1.8 (m, 8H). |

-continued

| Example | Spectrum |
|---|---|
| R | δ = 8.1–8.25 (m, 1H); 7.6–7.85 (m, 2H); 7.2–7.5 (m, 4H); 3.92 (s, 2H); 3.33 (s, 2H); 2.35 (s, 3H); 1.22 (s, 9H). |
| S | σ = 8.5 (br, 1H); 7.3–7.9 (m, 6H); 4.05 (br, 1H); 3.24 (s, 2H); 3.12 (m, 1H); 2.5–2.8 (m, 1H); 2.26 (t, J = 6.5 Hz, 2H); 1.6–2.0 (m, 6H); 1.56 (sect., J = 7 Hz, 2H); 0.99 (t, J = 7 Hz, 3H). |
| T | identical with S except: σ = 2.28 (ps.t, 2H); 1.3–1.7 (m, 4H); 0.91 (ps.t, 3H). |
| U | a δ = 8.2–8.35 (1 arom. H); 7.7–7.9 (2 arom. H); 7.3–7.6 (4 arom. H); 4.0 (s, 2H); 3.37 (s, 2H); 2.38 (s, 3H); 1.52 (s, 3H); 1.0–2.2 (11H). |
|  | b δ = 8.2–8.35 (1 arom. H); 7.7–7.9 (2 arom. H); 7.3–7.6 (4 arom. H); 5.76 (m, 2 olef. H); 3.91 (s, 2H); 3.13 (m, 2H); 2.25 (s, 3H); 1.23 (s, 3H); 0.8–2.0 (11H). |
| V | a δ = 8.15–8.35 (m, 1H); 7.7–7.9 (m, 2H); 7.3–7.6 (m, 4H); 3.95 (s, 2H); 3.35 (s, 2H); 2.35 (s, 3H); 1.8–2.3 (m, 1H); 2.0 (s, OH); 1.62 (d, J = 6.5 Hz, 2H); 1.53 (s, 3H); 1.04 u. 1.02 (2 d, J = 6.5 Hz, Σ 6H). |
|  | b δ = 8.2–8.4 (m, 1H); 7.7–7.9 (m, 2H); 7.3–7.6 (m, 4H); 5.78 (AB-portion of an ABX₂-system, 2 olef. H); 3.90 (s, 2H); 3.12 (m, 2H); 2.22 (s, 3H); 1.3–2.0 (m, 1H); 1.5 (s, OH); 1.4 (d, 2H); 1.3 (s, 3H); 0.92 u. 0.90 (2 d, J = 7 Hz, Σ 6H). |
| W | a δ = 8.2–8.35 (m, 1H); 7.7–7.9 (m, 2H); 7.3–7.6 (m, 4H); 3.98 (s, 2H); 3.36 (s, 2H); 2.38 (s, 3H); 2.1 (br, OH); 1.2–1.9 (m, 6H); 1.56 (s, 3H); 0.95 (ps.t., 3H). |
|  | b δ = 8.2–8.35 (m, 1H); 7.7–7.9 (m, 2H); 7.3–7.6 (m, 4H); 5.85 (AB-portion of an ABX₂-system, 2H); 3.90 (s, 2H); 3.12 (m, 2H); 2.25 (s, 3H); 1.2–1.7 (m, 6H + OH); 1.28 (s, 3H); 0.9 (ps.t., 3H). |
| X | a δ = 8.2–8.35 (m, 1H); 7.7–7.9 (m, 2H); 7.3–7.6 (m, 4H); 4.0 (s, 2H); 3.38 (s, 2H); 2.4 (s, 3H) 1.96 (br, OH); 1.54 (s, 3H); 1.14 (s, 9H). |
|  | b δ = 8.6–8.4 (m, 1H); 7.65–7.9 (m, 2H); 7.3–7.6 (m, 4H); 5.6–6.1 (AB-portion of an ABX₂-system, J = 15 + 2 × 5.5 Hz, 2H); 3.92 (s, 2H); 3.16 (d, 2H; J = 5.5 Hz); 2.25 (s, 3H); 1.4 (br, OH); 1.26 (s, 3H); 0.96 (s, 9H). |
| Y | a δ = 8.2–8.35 (m, 1H); 7.6–7.9 (m, 4H); 7.2–7.6 (m, 7H); 4.0 (s, 2H); 3.4 (s, 2H); 2.65 (br, OH); 2.4 (s, 3H); 1.85 (s, 3H). |
|  | b 8.15–8.35 (m, 1H); 7.65–7.9 (m, 2H); 7.2–7.6 (m, 9H); 5.6–6.1 (AB-portion of an ABX₂-system, J = 15 Hz + 2 × 5.5 Hz, 2H); 3.88 (s, 2H); 3.13 (d, J = 5.5 Hz, 2H); 2.24 (s, 3H); 2.0 (s, OH); 1.65 (s, 3H). |

I claim:
1. A compound in trans configuration of the formula:

$$R_2-\underset{R_3}{\underset{|}{C}}-\underset{R_4}{\underset{|}{N}}-CH-CH=CH-R_6 \quad \text{I}$$

with $R_1, R_4, R_5$ on the carbons.

wherein
$R_1$ is a radical of formula IIa,

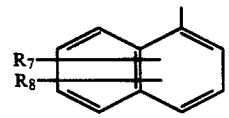

$R_2$, $R_3$, $R_5$, and $R_8$ are each hydrogen,
$R_4$ is methyl, and $R_6$ is a radical of formula IIIa $$-C\equiv C-R_{11} \qquad \text{IIIa}$$

where $R_{11}$ is alkyl of 2 to 6 carbon atoms or a chemotherapeutically acceptable acid addition salt thereof.

2. A compound as claimed in claim 1 the form of its hydrochloride.

3. A chemotherapeutical composition comprising an effective amount of a compound as claimed in claim 1 or a chemotherapeutically acceptable acid addition salt thereof in admixture with a chemotherapeutically acceptable diluent or carrier.

4. A method of treating diseases or infections caused by mycetes which comprises administering to a subject in need of treatment an effective amount of a compound as claimed in claim 1 or a chemotherapeutically acceptable acid addition salt thereof.

5. A compound according to claim 1 selected from the group in which $R_1$ is 1-naphthyl, $R_2$ is H, $R_3$ is H, $R_4$ is $CH_3$ and $R_5$, $R_6$ and the configuration are

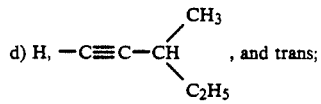

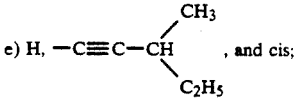

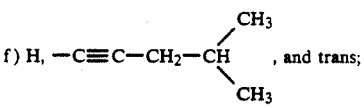

i) H, $-C\equiv C-(CH_2)_2-CH_3$, and trans;
j) H, $-C\equiv C-(CH_2)_4-CH_3$, and trans;
k) H, $-C\equiv C-(CH_2)_5-CH_3$, and trans;

or a chemotherapeutically acceptable acid addition salt thereof.

6. The compound according to claim 1 in which $R_1$ is 1-naphthyl, $R_2$ is H, $R_3$ is $CH_3$, $R_5$ is H, $R_6$ is

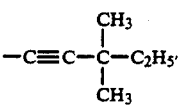

and the configuration is trans, or a chemotherapeutically acceptable acid addition salt thereof.

7. A compound according to claim 1 in which $R_{11}$ is alkyl of 3 to 5 carbon atoms.

8. A compound according to claim 1 in which $R_{11}$ is alkyl of 5 or 6 carbon atoms.

* * * * *

UNITED STATES PATENT AND TRADEMARK OFFICE
CERTIFICATE OF CORRECTION

PATENT NO.   : 5,132,459
DATED        : July 21, 1992
INVENTOR(S)  : Anton Stuetz It is certified that error appears in the above-identified patent and that said Letters Patent is hereby corrected as shown below:

Column 26,
Line 67, after "$R_2$, $R_3$, $R_5$," insert -- $R_7$ --.

Signed and Sealed this

Twenty-seventh Day of May, 2003

JAMES E. ROGAN
*Director of the United States Patent and Trademark Office*

Disclaimer

5,132,459—Anton Stuetz, Maria Enzersdorf, Austria. PROPENYLAMINES, PROCESSES FOR THEIR PRODUCTION, PHARMACEUTICAL COMPOSITIONS CONTAINING THEM AND THEIR USE AS PHARMACEUTICALS. Patent dated July 21, 1992. Disclaimer filed July 22, 2003, by the assignee, Novartis Pharmaceuticals Corporation.

The term of this patent shall not extend beyond the expiration date of Pat. No. 4,755,534.

*(Official Gazette, November 11, 2003)*